(12) United States Patent
Pellet et al.

(10) Patent No.: US 6,475,507 B1
(45) Date of Patent: Nov. 5, 2002

(54) SUSTAINED RELEASE COMPOSITIONS AND THE PROCESS FOR THEIR PREPARATION

(75) Inventors: Marc Pellet, Conde sur Iton (FR); Chantal Roume, Signes (FR)

(73) Assignee: Ipsen Pharma Biotech (FR)

( * ) Notice: Subject to any disclaimer, the term of this patent is extended or adjusted under 35 U.S.C. 154(b) by 0 days.

(21) Appl. No.: 09/707,372

(22) Filed: Nov. 6, 2000

Related U.S. Application Data

(62) Division of application No. 09/403,058, filed as application No. PCT/FR98/00773 on Apr. 17, 1998, now Pat. No. 6,217,893.

(30) Foreign Application Priority Data

Apr. 18, 1997 (FR) .............................................. 97 04837
Mar. 25, 1998 (FR) .............................................. 98 03666

(51) Int. Cl.$^7$ .............................. A61F 2/02; A61K 9/50; C07K 14/00
(52) U.S. Cl. ........................ 424/426; 424/400; 424/499; 424/501; 424/502; 530/350; 530/395
(58) Field of Search ................................ 424/426, 400, 424/499, 501, 502; 530/350, 395

(56) References Cited

U.S. PATENT DOCUMENTS

| | | | | |
|---|---|---|---|---|
| 5,021,554 A | * | 6/1991 | Thompson | 530/399 |
| 5,213,812 A | * | 5/1993 | Ruiz | 424/499 |
| 5,785,976 A | * | 7/1998 | Westesen et al. | 424/400 |
| 6,136,346 A | * | 10/2000 | Eljamal | 424/488 |
| 6,217,893 B1 | * | 4/2001 | Pellet et al. | 424/426 |

* cited by examiner

Primary Examiner—Christopher S. F. Low
Assistant Examiner—Abdel A. Mohamed
(74) Attorney, Agent, or Firm—Bierman, Muserlian and Lucas

(57) ABSTRACT

The invention relates to compositions in the form of microcapsules or implants comprising a biodegradable polymeric or copolymeric excipient or a mixture of such excipients with an inherent viscosity of between 0.5 dl/g and 1.6 dl/g in $CHCl_3$, and one active substance or a mixture of active substances, it being possible for said microcapsules or implants to release the active substance or mixture of active substances over a prolonged period of up to three months or more. These compositions may also comprise an active principle having a high specific surface area.

9 Claims, No Drawings

SUSTAINED RELEASE COMPOSITIONS AND THE PROCESS FOR THEIR PREPARATION

This application is a division of U.S. patent application Ser. No. 09/403,058 filed Oct. 13, 1999, now U.S. Pat. No. 6,217,893, which is a 371 of PCT/FR98/00773 filed Apr. 17, 1998.

The invention relates first of all to a composition in the form of microcapsules or implants comprising a biodegradable polymeric or copolymeric excipient or a mixture of such excipients with an inherent viscosity of between 0.5 dl/g and 1.6 dl/g in $CHCl_3$, and at least one active substance. The invention further relates to a composition in the form of microcapsules or implants comprising at least one biodegradable polymer or copolymer of high molecular weight and at least one water-soluble active substance of high specific surface area. Such compositions will be used to obtain a uniform release of the active substance over a prolonged period of up to more than three months.

BACKGROUND OF THE INVENTION

These compositions, and especially the microcapsules, are mainly used in pharmacy, but can also be employed in other sectors, particularly in agrochemistry, i.e. in the plant protection sector.

The value of administering active principles in the form of sustained release compositions has been known for a long time, whether they be conventional pharmaceutical products, for example steroids, peptides or proteins (cf., for example, U.S. Pat. No. 3,773,919 to Boswell), or products for use in plant protection. The formulations adopted can take the form of microparticles in which the active principle is incorporated in a biodegradable polymer or copolymer such as a polylactide/co-glycolide copolymer (PLGA).

It has been found that, especially when a relatively constant or, in any case, uninterrupted release mode is sought—this mode being referred to for example as "monophase" in European Patent EP 58 481—PLGA-type polymers of relatively low molecular weight, i.e. of low viscosity, are required. European patents EP 21 234 (cf. Example 8.B.2. describing a copolymer of intrinsic viscosity 0.5 dl/g), EP 52 510, in which a copolymer with a viscosity of 0.38 dl/g in hexafluoro-isopropanol (HFIP) is tested in vivo, and EP 26 599, which describes, by way of example, polymers with viscosities of 0.12 to 0.20 dl/g and claims polymers with a viscosity of 0.08 to 0.30 dl/g, may be mentioned in this connection. The polymers described in said patents are presented as producing constant release compositions. The compositions of Patent EP 26 599 can contain fertility control agents, for example.

It is moreover important to note in this respect that in the opposition proceedings relating to European Patent EP 58 481, which are still in progress on the date of filing of the present patent application, the Applicant limited its main claim to polymers of low viscosity (below 0.3 or 0.5 dl/g), which, according to the Applicant, are the only ones capable of permitting a release of the monophase type.

Furthermore, when a longer release period, for example of more than one month, is sought, more complex problems appear and a solution proposed by Patent EP 0 302 582, for example, consists in mixing several types of microcapsules made up of polymers of different viscosities.

BRIEF DESCRIPTION OF THE INVENTION

Now, the present Applicant has just found that certain polymers of high viscosity are suitable for the preparation of long-term sustained release compositions. It has also been found that the use of certain polymers produces compositions which have a very long-term monophase release profile without an initial period of no release (dead period). This applies particularly to polymers with an inherent viscosity preferably of at least 0.5 dl/g in $CHCl_3$ and more preferably of at least 0.6 or 0.7 dl/g. In principle, however, the inherent viscosity of these polymers will not exceed 1.6 dl/g ,in $CHCl_3$ and may be below 1.4 or 1.2 dl/g. Said polymers will preferably be PLGAs with a lactide/glycolide ratio varying from 40/60 to 90/10, and being preferably about 75/25.

DETAILED DESCRIPTION OF THE INVENTION

The polymers according to the invention can be prepared by the customary methods, especially by opening of the lactide or glycolide rings. Such a process is described for example in U.S. Pat. No. 3,773,919.

In the present invention it is also possible to use a mixture of polymers of different high viscosities, but compositions containing only one polymer or copolymer are preferred.

The invention therefore relates first of all to a composition in the form of microcapsules or implants comprising a biodegradable polymeric or copolymeric excipient or a mixture of such excipients with an inherent viscosity of between 0.5 dl/g and 1.6 dl/g in $CHCl_3$, and an active substance or a mixture of active substances, it being possible for these microcapsules or implants to release the active substance or mixture of active substances over a prolonged period of at least 1 month, preferably of at least 2 months and more preferably of at least 3 months.

Microcapsule is also understood to include microspheres, microparticles, nano-capsules, nanospheres or nanoparticles. Polymer will be understood as meaning a polymer, a copolymer or any mixture of these entities. Finally, active substance is understood as meaning an active substance, one of its salts, one of its precursors or any mixture of these compounds.

Salts of active substances which can be used for compositions according to the invention include especially the salts obtained from organic acids like acetic, malic, tartaric, oxalic, fumaric, citric, lactic, stearic, pamoic, methanesulphonic or p-toluenesulphonic acids, or from inorganic acids like hydrochloric, sulphuric, phosphoric or hydrobromic acids. It will be preferable to use a water-soluble product obtained by salification in the form of a cation, for example with acetic acid. However, it is possible to use an insoluble salt, for example a parnoate.

Particularly, the invention relates to a composition in the form of microcapsules or implants comprising a biodegradable polymeric or copolymeric excipient or a mixture of such excipients and an active substance or a mixture of active substances, said microcapsules or said implants being able to release the active substance or the mixture of active substances over a prolonged period of time of up to three months or more with an essentially monophase release profile, said composition being characterized in that:

either, when the composition is in the form of microcapsules:
  either the viscosity of said polymers or copolymers is comprised between 0.7 dl/g and 1.6 dl/g in $CHCl_3$ and the preparation process for said microcapsules does not comprise any stage of fusion of said microcapsules,
  or the viscosity of said polymers ou copolymers is comprised between 0.5 dl/g and 1.6 dl/g in $CHCl_3$ and said polymers or copolymers have an hydrophilic character;

or, when the composition is in the form of implants, the viscosity of said polymers or copolymers is comprised between 0.5 dl/g and 1.6 dl/g in $CHCl_3$. Preferably, the viscosity of the polymers or copolymers for the compositions according to the invention will be at least equal to 0.9 dl/g in $CHCl_3$.

The polymers or copolymers which can be used for the invention can be especially polymers such as those of lactic acid, glycolic acid, citric acid or malic acid, or else other biocompatible polymers like poly-β-hydroxybutyric acid, polyorthoesters, polyorthocarbonates, poly-α-cyanoacrylic acid esters, polyalkylene oxalates such as polytrimethylene or polytetramethylene oxalate, polyamino acids, etc. They can also be copolymers like PLGA, polystyrene, polymethacrylic acid, methacrylic acid/acrylic acid copolymers, polyamino acids, maleic anhydride polymers, ethyl cellulose, nitrocellulose, acetyl cellulose, etc. All these polymers or copolymers can be used by themselves or in any mixture. Generally, the PLGAs will comprise from 40 to 90% of lactide and from 10 to 60% of glycolide. It will be preferable to use D,L-PLGA and more preferable to use a D,L-PLGA produced from 70 to 80% of DL-lactide and 20 to 30% of glycolide. A PLGA synthesized from 75% of DL-lactide and 25% of glycolide will be particularly suitable for the invention.

Another particularly preferred polymer for the invention is L-PLGA obtained from L-lactide and glycolide. Compared with D,L-PLGA of the same viscosity, L-PLGA assures a slower release and represents an alternative to the D,L-PLGAs of higher viscosity.

In a general manner, the polymers or copolymers possessing a hydrophilic character will be preferred. Hence, preference will generally be given to the PLGAs obtained by ring opening with hydrophobic initiators such as those of the lauryl alcohol type, those obtained by ring opening with hydrophilic initiators such as those of the lactic acid or glycolic acid type.

By polymer or copolymer possessing a hydrophilic character, it is meant a polymer or copolymer for which the terminal chain is polar (for example, this terminal chain includes at its end an acidic function), by opposition to a polymer or copolymer possessing a hydrophobic character for which the terminal chain is apolar (for example, this terminal chain is an aliphatic chain).

The acid number, which corresponds to the number of milliequivalents of KOH required per gram of polymer to neutralize the free acidity, seems to be the parameter which correlates best with the hydrophilic or hydrophobic character of a polymer or copolymer. Wherever the terminal chains of the polymers or copolymers may include a free acidic function, owing to the nature of the monomer, this acid number may be measured.

In a general manner, the Applicant has found that the hydrophilic polymers produce a better release profile. Hence, the acid number of the polymers used for the invention will preferably be at least equal to 1, or better, 1.2, and more preferably at least equal to 1.5 or 2.

The core loading of the microcapsules according to the invention, i.e. the ratio of the weight of encapsulated pure peptide to the total weight of the microcapsule, will generally be between 0 and 20% and preferably between 2 and 15%. In the case of triptorelin acetate, the loading will preferably be less than or equal to 10% and more preferably between 4 and 8% for forms which permit release over a period of about 3 months. In the case of lanreotide acetate, the loading will preferably be between 10 and 20%.

In the case of implants, the core loading will generally be between 0 and 30% and preferably between 15 and 25%.

The encapsulation step can be a so-called coacervation step, such as that described in U.S. Pat. No. 3,773,919 or European Patent EP 52 510.

It is also possible to use a so-called melting-extrusion process such as that described in European Patent EP 58 481 or U.S. Pat. No. 5,225,205, the products obtained then optionally being ground by the customary methods to give microparticles.

In another respect, a water-soluble active principle such as a water-soluble salt of a peptide, for example the acetate, can be used. It is also possible to use an insoluble salt of a soluble molecule, such as a fatty acid salt of a peptide, for example a peptide pamoate such as that described in British Patent GB 2 209 937.

The compositions obtained by melting-extrusion using the polymers according to the invention can also be presented in the form of implants and be used as such.

These implants are preferably small (mini-implants or microimplants) with a diameter of the order of 1 mm, for example of between 0.8 and 1.2 mm. The length of these implants can be for example between 10 and 35 mm, for example of the order of 25 mm. These implants give very advantageous results with low doses of active principle, for example of the order of 3 mg of triptorelin acetate per implant. Such implants can release the active principle over a period of up to 3 months.

Moreover, it has been found that the form of the active principle can also influence the diffusion of this product. In particular, if an active principle can be obtained in a crystalline or amorphous form, it is not arbitrary which of the two forms is chosen.

Patent application EP 709 085 describes microcapsules comprising a polymer and an amorphous water-soluble active substance. It is particularly concerned with the importance of obtaining small particles of active substance, preferably with a size of less than 10 m. However, this patent application does not disclose any process for the preparation of said particles and no mention is made of the effect of the specific surface area of the particles of active principle on the release profile of the compositions containing these particles. Now, the Applicant has already been using, since 1986, microcapsules containing an amorphous active substance, namely triptorelin acetate, sold under the name Decapeptyl 3.75 mg, which has a particle size of only about 8 m. However, it has found that the particle size is not the only determining parameter for favouring release over a prolonged period of up to more than three months or more.

In principle, the question of amorphous character does not arise for products such as peptides or proteins, whose method of preparation, especially lyophilization, leads to an amorphous product in the majority of cases, as for Decapeptyl 3.75 mg.

There are copious illustrations of this phenomenon in the literature and the following articles may be mentioned in particular: Hsu, C.C. et al., *Pharmaceutical Research*, 12 (1), 69–77 (1995) or Towns, J. K., *Journal of Chromatography, A*, 705 (1), 115–27 (1995).

The invention therefore also relates to a composition in the form of microcapsules or implants comprising at least one biodegradable polymer or copolymer of high molecular weight and at least one water-soluble active substance of high specific surface area. Particularly, said specific surface area is greater than 2 $m^2/g$, and preferably greater than 3 $m^2/g$. More preferably, said specific surface area is greater than 5 $m^2/g$ or 10 $m^2/g$. Even more preferably, said specific surface area is greater than 20 $m^2/g$, and preferably greater than 30 $m^2/g$.

The invention relates preferably to the above compositions in which the water-soluble active substance is a protein or a peptide.

It further relates to the above compositions for which the polymer or copolymer viscosity is comprised between 0.5 and 1.6 dl/g in $CHCl_3$, and preferably comprised between 0.9 and 1.6 dl/g in $CHCl_3$. Particularly, polymers or copolymers of viscosity comprised between 0.7 and 1.3 dl/g in $CHCl_3$ may be chosen and more preferably polymers or copolymers of viscosity comprised between 0.7 and 1.3 dl/g. PLGAs are particularly adapted for the invention. Preferably, said PLGAs will be produced from 40 to 90% lactide and 10 to 60% glycolide, and more preferably from 70 to 80% lactide and 20 to 30% glycolide. The hydrosoluble active substances incorporated in the microcapsules or implants will preferably be proteins or peptides.

Compositions comprising an active substance of high specific surface area will preferably be such that viscosity of the polymer or copolymer is comprised between 0.5 and 1.6 dl/g in $CHCl_3$ and that the polymer or copolymer presents an hydrophilic character, the acid number of the latter being greater than 1 meq KOH per gram of polymer or copolymer, and preferably greater than 1.2, more preferably 1.5 mEq or even 2 meq KOH per gram of polymer or copolymer.

The invention further relates to compositions in the form of microcapsules or implants comprising an active substance of high specific surface area characterized in that the polymer or copolymer is a PLGA, and preferably a PLGA produced from 70 to 80% lactide and 20 to 30% glycolide, the viscosity of said PLGA being comprised between 0.5 and 1.6 dl/g on $CHCl_3$ and the active substance incorporated in the microparticles or implants being a protein or a peptide.

These microcapsules or implants permit a monophase release profile in which the initial peak (or burst) is reduced in comparison with certain other preparations using a polymer of lower molecular weight, so they make it possible to release the active substance over a prolonged period of up than three months or more.

In other words, the Applicant has found that the release properties, notably the monophase type release, of compositions in the form of microcapsules or implants, particularly of compositions based on PLGA and including as an active principle a peptide or a protein, are considerably improved if at least one of the following characteristics is present:

a) the polymer or copolymer is a PLGA which presents a viscosity in chloroform of at least 0.5 dl/g, preferably of at least 0.9 dl/g and in principle lower than 1.6 dl/g;

b) the polymer or copolymer is a PLGA which is prepared from 70 to 80% lactide and from 20 to 30% glycolide;

c) the polymer or copolymer presents an hydrophilic character, and preferably has an acid number greater than I mEq KOH, and m ore preferably greater than 1.2 or even 1.5 mEq KOH per gram of polymer or copolymer;

d) the active principle, preferably a peptide or a protein, has a high specific surface area and greater than 2 $m^2/g$, preferably greater than 10 $m^2/g$, more preferably greater than 20 $m^2/g$ or even greater than 30 $m^2/g$;

these characteristics being optionally combined with the use of a L-PLGA instead of a D,L-PLGA.

According to its present knowledge, the Applicant is of the opinion that characteristic d) taken alone is very important-[]and may be advantageously combined to the other characteristics a) b) or c). Particularly, the characteristic d) may be combined to following characteristics : a) alone, b) alone, c) alone, a) and b) together, a) and c) together, b) and c) together, or a), b) and c) together. More preferably, characteristic d) will be combined at least with characteristic c).

Among the active substances which can be used for the different aspects of the invention, there may be mentioned in particular proteins and peptides. Said active substances can be selected for example from the group consisting of the following substances: triptorelin or one of its salts, particularly triptorelin acetate, lanreotide or one of its salts, particularly lanreotide acetate, octreotide or one of its salts (as described for example in European Patent EP 29 579), particularly octreotide acetate or pamoate, a compound with LH-RH activity, such as triptorelin, goserelin, leuprorelin, buserelin or their salts, an LH-RH antagonist, a GPIIb/IIIa antagonist, a compound with a similar activity to a GPIIb/IIIa antagonist, erythropoietin (EPO) or one of its analogues, the various types of interferon-α, interferon-β, or -γ, somatostatin, a somatostatin derivative such as that described in European Patent EP 215 171, a somatostatin analogue such as that described in U.S. Pat. No. 5,552,520 (this patent itself includes a list of other patents describing somatostatin analogues, which are incorporated in the present patent application by way of reference), insulin, a growth hormone, a growth hormone releasing factor (GRF), a growth hormone releasing peptide (GHRP), an epidermal growth factor (EGF), a melanocyte stimulating hormone (MSH), a thyrotropin releasing hormone (TRH) or one of its salts or derivatives, a thyroid stimulating hormone (TSH), a luteinizing hormone (LH), a follicle stimulating hormone (FSH), a parathyroid hormone (PTH) or one of its derivatives, a lysozyme hydro chloride, a parathyroid hormone related peptide (PTHrp), an N-terminal peptide fragment (position 1→34) of human PTH hormone, vasopressin or one of its derivatives, oxytocin, calcitonin, a calcitonin derivative with a similar activity to that of calcitonin, a calcitonin gene related peptide (CGRP), glucagon, a peptide similar to glucagon (GLP), gastrin, a gastrin releasing peptide (GRP), secretin, pancreozymin, cholecystokinin, angiotensin, human placental lactogen, human chorionic gonadotropin (HCG), enkephalin, an enkephalin derivative, colony stimulating factor (CSF), endorphin, kyotorphin, interleukins, for example interleukin-2, tuftsin, thymopoietin, thymosthymlin, thymic humoral factor (THF), thymic serum factor (TSF), a derivative of thymic serum factor (TSF), thymosin, thymic factor X, tumour necrosis factor (TNF), motilin, bombesin or one of its derivatives as described in U.S. Pat. No. 5,552,520 (this patent itself includes a list of other patents describing bombesin derivatives, which are incorporated in the present patent application by way of reference), prolactin, neurotensin, dynorphin, caerulein, substance P, urokinase, asparaginase, bradykinin, kallikrein, nerve growth factor, a blood clotting factor, polymixin B, colistin, gramicidin, bacitracin, a protein synthesis stimulating peptide, an endothelin antagonist or one of its salts or derivatives, a vasoactive intestinal polypeptide (VIP), adrenocorticotropic hormone (ACTH) or one of its fragments, a platelet derived growth factor (PDGF), a bone morphogenetic protein (BMP), a pituitary adenylate cyclase activating polypeptide (PACAP), neuropeptide Y (NPY), peptide YY (PYY), a gastric inhibitory polypeptide (GIP) and polynucleotides, especially double-stranded RNAs (ds-RNAs) such as those described in Patent application EP 0 300 680 or French Patent no. 2 622 586.

ds-RNA is preferably understood as meaning polyadenylic acid complexed with polyuridylic acid, which is also called poly(A)-poly(U) or Poly-adenur. Other ds-RNAs can be used for the invention, especially a complex of polyinosinic acid with polycytidylic acid, which is also known by the name poly(I)-poly(C), as well as these same complexes modified by the introduction of uridylic acid into the polycytidylic acid chain, such as the product Ampligen from the HEMISPHERx company (for a description of these products, reference may be made especially to European Patent application EP 0 300 680). The ds-RNA used can be for example a mixture of ds-RNAs as defined above. The ds-RNAs are preferably prepared by the process described in French Patent no. 2 622 586.

A high specific surface area can be obtained for the previously mentioned substances as soon as they are water-soluble or transformed into water-soluble substances, for example by salification or grafting of a water-soluble chain on their structure. This is particularly valid for the previously mentioned peptides and proteins. Any other water-soluble active substance or one of its salts or precursors, and particularly the salts obtained by salification with acetic acid, may also be used by a person skilled in the art for this aspect of the invention if they consider it appropriate.

According to one of the preferred aspects of the invention, the peptide or protein with a high specific surface area are chosen from the group consisting of triptorelin acetate, lanreotide acetate or octreotide acetate.

Peptide and/or protein are understood in the present application as meaning both the peptide and/or the protein themselves and pharmacologically active fragments, salts or derivatives of these peptides or proteins.

The water-soluble active substance as used to manufacture microcapsules or implants according to the invention, and particularly triptorelin acetate, lanreotide acetate, octreotide acetate, goserelin, leuprorelin, buserelin or their salts, is preferably obtained by a process which principally involves two steps:
- a lyophilization step comprising the rapid immersion of a dilute solution of the water-soluble substance in a medium whose temperature is below −50° C., and preferably below −70° C.; and
- optionally a grinding step, which will preferably comprise ultrasonic grinding.

Dilute solution of the active substance is understood as meaning a solution whose concentration of said active substance is less than half the saturation concentration and preferably less than a quarter of said saturation concentration when the latter is at least equal to at least 200 g/l. This process produces an active substance of high specific surface area.

Rapid immersion must be understood as meaning contact with a low temperature medium, causing instantaneous freezing of the solution of water-soluble substance.

For the lyophilization, the solution may be frozen for example in a tray floating in a tank of liquid nitrogen, before the actual lyophilization is carried out.

Preferably, in order to obtain a maximum specific surface area, the rapid immersion of the solution will be preceded by a micronization of the solution of active substance. When the solution of active substance is micronized beforehand, the temperature of the low temperature medium may only be below −50° C.

For example, to obtain a very high specific surface area, it may be chosen to atomize the solution by spraying it through an atomizer onto a metal plate at very low temperature. The temperature of the plate will preferably be below −50° C. and more preferably below −70° C. or even −80° C. or −120° C. This temperature may be reached for example by immersing a metal plate in a very low temperature medium, for example liquid nitrogen. According to one preferred variant of the invention, the metal plate is hollow and the solution is sprayed inside said plate by means of an atomizer.

Other freezing techniques can be considered, for example-atomization of the solution of active substance into a precooled bath of a non-solvent for said active substance. The non-solvent will preferably be a liquefied gas, such as for example liquid nitrogen.

Another possibility is to freeze the active substance solution on a rotating plate (drum freezing). As previously indicated, this freezing will preferably be preceded by a micronization of the active substance solution.

When the process of freezing in a tray is applied to an active substance in order to prepare sustained release microcapsules or implants according to the invention, the specific surface area of the active substance, after lyophilization but before grinding, will preferably be greater than 2 $m^2/g$. The specific surface area of the active substance will more preferably be greater than 3 $m^2/g$ or even 5 $m^2/g$.

If a specific surface area greater than 10 $m^2/g$ is required, the process which includes a micronization step will preferably be employed. The specific surface area obtained for the active substance after lyophilization will preferably be greater than 15 $m^2/g$. This specific surface area will even more preferably be greater than 20 $m^2/g$ or even 30 $m^2/g$.

The specific surface areas obtained may be varied by varying the freezing conditions of the solution of active substance by way of different parameters, such as for example the freezing rate or the concentration of the solution.

The specific surface area of the active substance is a favourable factor for obtaining release over a prolonged period, particularly in the case of microcapsules. In fact, as already mentioned, particles of an active substance which have the same size but different specific surface areas will give totally different results with the same polymeric excipient.

The invention therefore also relates to the processes as described above, applied to a biologically active water-soluble substance. It further relates to the biologically active water-soluble substance as obtained by these processes, said substance having a high specific surface area.

Particularly, the invention relates to triptorelin acetate, lanreotide acetate or octreotide acetate as obtained by the previously described processes, or to a double strand RNA, preferably polyadenylic acid complexed with polyuridylic acid as obtained by these processes.

As indicated above, the compositions according to the invention are preferably used in the pharmaceutical sector. The pharmaceutical compositions can be administered to a patient by different routes, however, the preferred route is subcutaneous or intra-muscular injection. The microcapsules according to the invention can first be suspended in a vehicle appropriate for injection, such as an aqueous solution of sodium chloride or an aqueous solution of mannitol.

Unless defined otherwise, all the technical and scientific terms used here have the same meanings as those commonly understood by an ordinary specialist in the field to which this invention belongs. Likewise, all the publications, patent applications, patents and any other references mentioned here are incorporated by way of reference.

The following examples are presented in order to illustrate the above procedures and must not under any circumstances be considered as limiting the scope of the invention.

EXAMPLES

For all these examples, the inherent viscosities (IV) were measured by the conventional methods of flow time measurement, as described for example in "Pharmacopoée Européenne", 1997, pages 17–18 (capillary tube method). Unless stated otherwise, these viscosities have been measured in chloroform at a concentration of 0.1% at 25° C. or in hexaisofluoropropanol at a concentration of 0.5% at 30° C. Where measured, the specific surface area of the active substance was determined by the so-called BET method (absorption of a nitrogen monolayer on the active substance), a method well known to a person skilled in the art.

For the following examples, a peptide which has undergone the lyophilization process according to the invention will be called the "modified" peptide, in contrast to the "unmodified" peptide, which is lyophilized in conventional manner (without sudden immersion at low temperature).

Example 1

16.620 g of "unmodified" triptorelin acetate are dissolved in 554 ml of water. The solution is frozen in a tray floating in a tank of liquid nitrogen, then lyophilized.

15.18 g of "modified" triptorelin acetate are thus obtained with a yield of 91.34%. This compound has a specific surface area of 4.7 m$^2$/g, compared with 0.8 m$^2$/g before lyophilization.

The triptorelin acetate is then subjected to ultrasonic grinding: 15 minutes are sufficient to obtain particles smaller than 10 m with the modified peptide (whereas 30 minutes are required to obtain this particle size with the unmodified peptide).

The encapsulation step is then performed by the coacervation method as described in European Patent EP 52 510 and U.S. Pat. No. 3,773,919, starting from 3.378 g of this ground modified triptorelin acetate and a 7.30% solution of D,L-PLGA (D,L-PLGA composed of 75% of DL-lactide and 25% of glycolide, inherent viscosity in chloroform=0.70 dl/g, acid number=1.61 meq KOH/g) in dichloromethane. 390 ml of silicone oil were added in order to form microcapsules by the coacervation process. These microcapsules are recovered after immersion in a bath of heptane (22 l) and filtration on a 10 m membrane.

Example 2

0.338 g of unmodified triptorelin acetate, with a particle size of 8 m after ultrasonic grinding for 30 minutes, was added, with stirring, to a 7.30% solution of D,L-PLGA in dichloromethane (PLGA equivalent to that described in Example 1). 40 ml of silicone oil were added in order to form microcapsules, which were subsequently precipitated in a bath of heptane (2 l) and then filtered on a 10 m membrane.

Examples 3 to 6

0.338 g of triptorelin acetate modified under the conditions described in Table no. 1 below was added, after ultrasonic grinding, to a 7.30% solution of a 33.3%/33.3%/33.3% mixture of three D,L-PLGAs (having the characteristics described in Table no. 2 below) in dichloromethane. 40 ml of silicone oil were added in order to form microcapsules, which were subsequently precipitated in a bath of heptane (2 l) and then filtered on a 10 m membrane.

TABLE NO. 1

| Example | Concentration (g/l) | Amount of triptorelin acetate (g) | Amount of water (ml) | Specific surface area (m$^2$/g) |
|---|---|---|---|---|
| 3 | 200 | 3 | 15 | 4.4 |
| 4 | 150 | 3 | 20 | 4.7 |
| 5 | 100 | 3 | 30 | 4.8 |
| 6 | 50 | 3 | 60 | 7.3 |

The specific surface area of the (unmodified) starting triptorelin acetate is 0.8 m$^2$/g.

The physicicochemical characteristics of the three mixed polymers are collated in Table no. 2 below:

TABLE NO. 2

| Characteristic | PLGA no. 1 | PLGA no. 2 | PLGA no. 3 |
|---|---|---|---|
| Lactide/glycolide ratio | D,L-PLGA 50:50 | D,L-PLGA 75:25 | D,L-PLGA 75:25 |
| Inherent viscosity in CHCl$_3$ (dl/g) | 0.47 | 0.61 | 0.70 |
| Acid number (meq KOH/g) | 2.68 | 2.08 | 1.61 |

Example 7

22.560 g of unmodified lanreotide acetate are dissolved in 752 ml of water. The solution is frozen in a tray floating in a bath of liquid nitrogen, and then lyophilized. 21.75 g of modified lanreotide acetate with a specific surface area equal to 4.4 m$^2$/g are obtained with a yield of 96.41%.

The encapsulation step is then performed by the coacervation method as described in European Patent EP 52 510 and U.S. Pat. No. 3,773,919, starting from 7.5 g of this ground modified triptorelin acetate and a 3.7% solution of D,L-PLGA (D,L-PLGA composed of 50% of DL-lactide and 50% of glycolide, inherent viscosity in HFIP=0.55 dl/g) in dichloromethane. 650 ml of silicone oil were added in order to form microcapsules by the coacervation process. These microcapsules are recovered after immersion in a bath of heptane (30 l) and filtration on a 10 m membrane.

Examples 8 and 9

Microcapsules of triptorelin acetate were manufactured with D,L-PLGA (D,L-PLGA composed of 75% of DL-lactide and 25% of glycolide) of different weight average molecular weights (Mw). They were manufactured by the process described in Example 1 using a triptorelin acetate with a specific surface area of 4.7 m$^2$/g.

The physicochemical parameters of Examples 8 and 9 are collated in the table below:

| Example | Mw THF | IV CHCl$_3$ (dl/g) | Acid number (meq KOH/g) |
|---|---|---|---|
| 8 | 58,400 | 0.61 | 2.08 |
| 9 | 132,650 | 0.93 | 1.31 |

Example 10

Microcapsules were manufactured according to the process described in Example 1 using D,L-PLGA (D,L-PLGA composed of 75% of DL-lactide and 25% of glycolide; molecular weight determined in THF: 80,100; viscosity in chloroform: 0.75 dl/g, acid number=0.40 meq KOH/g) having a hydrophobic tendency.

Example 11

Microcapsules were manufactured according to the process described in Example 1, starting from an L-PLGA (L-PLGA composed of 75% of L-lactide and 25% of glycolide; molecular weight in THF: 99,260; viscosity in chloroform: 0.78 dl/g, acid number=1.80 meq KOH/g) having a crystalline tendency.

Example 12

One part by weight of triptorelin acetate is added to four parts by weight of powdered D,L-PLGA (PLGA composed of 75% of lactide and 25% of glycolide; molecular weight determined in THF: 103,810; inherent viscosity in chloroform: 0.82 dl/g).

The lumps are destroyed by sieving on a 400 m mesh, the product is mixed for 20 minutes at 42 rpm and the mixture is extruded at 120γ C. through a die of diameter 1 mm on a screw extruder. The extrudate is then cooled in air and sized by drawing (drawing device) to a final diameter of 0.85 mm.

The concentration of the mixture per unit length (mm) is determined and the rods of extrudate are cut to calculated lengths (in this case 24 mm) so that the microimplants contain a 3 mg dose of triptorelin. Finally, the weight of each microimplant is checked.

Examples 13 and 14

The same protocol is used for these two examples:

5 g of lanreotide acetate are dissolved in water in order to give the solution the chosen concentration (for example, to obtain a concentration of 30 g/l, 167 ml of sterile water are added). This solution is atomized with a 500 ml sprayer whose jet is adjusted so as to give the finest possible droplets. The droplets obtained are sprayed into a tray, the bottom of which is immersed in liquid nitrogen. Two temperature probes are introduced into the tray beforehand so that the change in the temperature of the product can be monitored.

Once the product is frozen, the tray is introduced into a lyophilizer whose plate is at about −54° C.

The temperature of the products and that of the plate are left to equilibrate for 1 hour. This leads on to the sublimation stage (the temperature of the plate is set at 20γ C. and the pressure in the tank at 100 bar). This stage lasts about 30 hours. The mean final temperature of the product is 13γ C. The secondary desiccation which follows (pressure of 50 bar in the tank) lasts about 24 hours. The mean final temperature of the product is 20γ C.

The characteristics of the reactants used and the products obtained are summarized in the table below:

| Characteristics | Example 13 | Example 14 |
|---|---|---|
| Weight of lanreotide acetate used (g) | 5.00 | 5.00 |
| Concentration of the solution (g/l) | 30 | 10 |
| Weight of lanreotide acetate recovered (g) | 4.54 | 4.10 |
| Specific surface area obtained (m²/g) | 36 | 43 |

The lanreotide acetate of specific surface area 43 m²/g obtained previously (Example 14) is incorporated into microcapsules according to the following process:

0.782 g of lanreotide acetate is weighed into a glass tube. 15 ml of dichloromethane are added to the peptide salt. The peptide is subjected to ultrasonic grinding by means of an ultrasonic generator equipped with an amplifier and a dipping or flat ended probe (frequency=50 Hz, power=250 W; grinding lasts about 15 min).

The encapsulation step is then performed according to the coacervation method as described in European Patent EP 52 510 and U.S. Pat. No. 3,773,919, using the 0.782 g of ground lanreotide acetate and a solution of 4 g of 50:50 D,L-PLGA (IV=0.48 dl/g in CHCl₃) in 35 ml of dichloromethane. 34.2 ml of silicone oil were added in order to form microcapsules by the coacervation process. These micro-capsules are recovered after immersion in a bath of heptane (2.5 l) and filtration on a 10 m membrane.

The microspheres obtained can then be dried under vacuum, divided up into bottles and lyophilized with excipients (for example ballast or a surfactant) to enable storage under good conditions and to facilitate suspension of the microcapsules.

Examples 15 and 16

A protocol similar to the one of Example 1 is used for these two examples. The peptide used is the same as that of these examples. The characteristics in terms of used PLGA, amount of peptide used (for these examples, modified triptorelin acetate) and preparation parameters of the microcapsules are listed in the table below:

| Characteristics | Example 15 | Example 16 |
|---|---|---|
| Weight of modified triptorelin acetate used (g) | 2.58 | 2.58 |
| Quantity of polymer used (g) | 30 | 30 |
| Quantity of silicone oil used (ml) | 600 | 650 |
| Quantity of dichloromethane used (ml) | 812 | 812 |
| Lactide/glycolide ratio | 75/25 | 75/25 |
| Viscosity of the PLGA in CHCl₃ (dl/g) | 0.93 | 0.96 |
| Measured acid number | 1.22 | 1.12 |

Study of the Release Profiles of Microcapsules According to the Invention

In order to illustrate the value of microcapsules according to the invention, their release profiles were studied in vitro.

For each of Examples 1 to 11 and 15 to 16, the release from three samples of about 25 mg of microcapsules (about 20 mg for Example 7), placed in 4 ml of 0.9% sodium chloride solution, is measured. Extraction is carried out after 1 hour, 1 day and 4 days of release into the solution, maintained at 37γ C.

The triptorelin is determined by high performance liquid chromatography (HPLC), relative to a calibration range, in gradient mode in a trifluoroacetic acid (TFA) system. To obtain the standard calibration range for triptorelin, a solution $T_1$ is prepared as follows: a sample of about 7.5 mg of reference triptorelin acetate is placed in a 50 ml flask; it is made up to 50 ml with 0.1% acetic acid solution. Solutions $T_2$ and $T_3$ are prepared from solution $T_1$ as follows: for $T_2$, 10 ml of solution $T_1$ are taken and made up to 20 ml with 0.1% acetic acid solution. For solution $T_3$, 1 ml of solution $T_1$ is taken and made up to 50 ml with 0.1% acetic acid solution.

The lanreotide is determined in a similar fashion by HPLC. To obtain the standard calibration range for lanreotide, a solution T'$_1$, is prepared as follows: a sample of about 16.5 mg of reference triptorelin acetate is placed in a 50 ml flask; it is made up to 50 ml with 0.1% acetic acid solution. Solutions T'$_2$, T'3, T'4 and T'5 are prepared from solution T'$_1$ as follows: for T'2, 10 ml of solution T'$_1$ are taken and made up to 25 ml with 0.1% acetic acid solution. For solution T'3, 5 ml of solution T'$_1$ are taken and made up to 25 ml with 0.1% acetic acid solution. Solution T'4 is obtained by dilution of 2 ml of solution T'1 in a 0.1% acetic acid solution in order to obtain a total volume of 25 ml, and solution T'5 by dilution of 1 ml of solution T'1 in a 0.1% acetic acid solution in order to obtain a total volume of 25 ml.

The amount of triptorelin acetate or lanreotide acetate released is determined as a percentage relative to the amount of triptorelin acetate or lanreotide acetate initially present (100%), which serves as the reference.

The result of the in vitro tests are summarized in the table below:

| Examples | Cumulative amount released (%) | | |
|---|---|---|---|
| | 1 hour | 1 day | 4 days |
| 1 | 8 | 16 | 27 |
| 2 | 9 | 47 | 57 |
| 3 | 10 | 45 | 67 |
| 4 | 10 | 37 | 65 |
| 5 | 9 | 41 | 66 |
| 6 | 8 | 30 | 55 |
| 7 | 3 | 14.5 | 28.3 |
| 8 | 11 | 40 | 67 |
| 9 | 2 | 4 | 6 |
| 10 | 5 | 12 | 14 |
| 11 | 1 | 2 | 2 |
| 15 | 2 | 4 | 13 |
| 16 | 2 | 5 | 10 |

The results of the in vivo tests correlate perfectly with those of the in vitro tests. By way of example, microcapsules of Example 1 were injected intramuscularly into rats at a dose of 1.2 mg/kg. A plasma analysis revealed that the amount of triptorelin remained constantly above 0.1 mg/ml over a period of more than 90 days. The same studies conducted on microcapsules of Example 2 showed that the amount of testosterone remained constantly below 1 ng/ml over a period of more than 90 days. Furthermore, microcapsules of example 9 have been injected intramuscularly into rats at a dose of 1.2 mg/kg and a plasma analysis revealed that the amount of triptorelin remained constantly above 0.1 ng/ml over a period of more than 90 days.

The microplants of Example 12 were tested in vivo as follows: a total dose of 3 mg of triptorelin was injected intramuscularly into 6 beagle dogs (weighing about 12 kg), into a muscle was injected of the back paw of each of the animals. A plasma analysis revealed that the amount of triptorelin remained constantly above 0.1 ng/ml over a period of more than 90 days.

What is claimed is:

1. A process for the preparation of a water-soluble substance of high specific surface area comprising:

a lyophilization step in which the freezing step is carried out by spraying a dilute solution of the water-soluble substance onto a metal plate having a temperature below −50° C. to effect instantaneous freezing.

2. The process of claim 1 wherein the medium temperature is below −70° C.

3. The process of claim 2 wherein the water-soluble substance is a protein or a peptide.

4. The process of claim 1 which further comprises a grinding step wherein the lyophilized water-soluble substance is ground.

5. The process of claim 1 wherein the dilute solution has a concentration of less than half saturation concentration.

6. The process of claim 5 wherein the saturation concentration is at least 200 g/l of water-soluble substance and the dilute solution is less than one quarter of saturation concentration.

7. The process of claim 1 wherein the dilute solution is first subjected to a micronization step being sprayed onto the metal plate.

8. The process of claim 7 wherein the micronization is effected by passing the dilute solution through an atomizer.

9. The process of claim 7 wherein the metal plate is hollow and the solution is sprayed inside said plate.

\* \* \* \* \*